US011052324B2

(12) United States Patent
Piszczek et al.

(10) Patent No.: US 11,052,324 B2
(45) Date of Patent: Jul. 6, 2021

(54) ADVANCED PROCESS CONTROL SCHEME FOR DIVIDING WALL COLUMN AND DUAL-DIVIDING WALL COLUMN WITH MULTIPLE PRODUCTS

(71) Applicant: ExxonMobil Research and Engineering Company, Annandale, NJ (US)

(72) Inventors: Robert Piszczek, Spring, TX (US); Philippe D'Hooghe, Merelbeke (BE); David A. Hokanson, Houston, TX (US); Erik Kluwen, Ridderkerk (NL)

(73) Assignee: ExxonMobil Research & Engineering Company, Annandale, NJ (US)

( * ) Notice: Subject to any disclaimer, the term of this patent is extended or adjusted under 35 U.S.C. 154(b) by 0 days.

(21) Appl. No.: 16/545,172

(22) Filed: Aug. 20, 2019

(65) Prior Publication Data

US 2020/0087229 A1 Mar. 19, 2020

Related U.S. Application Data (60) Provisional application No. 62/731,296, filed on Sep. 14, 2018.

(51) Int. Cl.
*B01D 3/14* (2006.01)
*C10G 7/12* (2006.01)
*C07C 7/04* (2006.01)

(52) U.S. Cl.
CPC ............. *B01D 3/141* (2013.01); *B01D 3/143* (2013.01); *C07C 7/04* (2013.01)

(58) Field of Classification Search
CPC .......... B01D 3/141; B01D 3/143; B01D 3/42; B01D 3/4205; B01D 1/0082; C07C 7/04; C10G 7/12
See application file for complete search history.

(56) References Cited

U.S. PATENT DOCUMENTS

| 6,106,674 A | 8/2000 | Agrawal et al. |
| 6,291,734 B1 | 9/2001 | Stork |

(Continued)

FOREIGN PATENT DOCUMENTS

| EP | 1321175 A2 | 6/2003 | |
| EP | 1681094 A2 * | 7/2006 | ............ B01D 3/141 |
| WO | WO2017103776 A1 * | 6/2017 | ............... C07C 7/08 |

OTHER PUBLICATIONS

Tututi-Avila, S. et al. (2017). Dividing-wall columns: Design and control of a kaibel and a satellite distillation column for BTX separation. Chemical Engineering and Processing: Process Intensification, 114, 1-15. (Year: 2017).*

(Continued)

*Primary Examiner* — Jonathan Miller
*Assistant Examiner* — Gabriel E Gitman
(74) *Attorney, Agent, or Firm* — Glenn T. Barrett (57) ABSTRACT

Systems and methods are provided for improving process control of separation systems that include one or more dividing walls within a single column. It has been discovered that improved process control can be achieved by controlling the dividing wall columns based on energy balance instead of mass balance. The energy balancing can be performed in part based on controlling temperature at a plurality of locations on the feed side within a first divided portion of the column. Using energy balancing based on temperature control at a plurality of locations on the feed side can facilitate maintaining the operation of the dividing wall columns within a single region of phase space that can be suitably approximated by linear models. This can allow conventional process controllers to manage the manipulated and controlled variables. In addition to controlling the temperature at a plurality of locations on the feed side, a plurality of other characteristics can be used as manipulated (Continued)

or controlled variables. Optionally, a multivariable controller can be used to provide further improved control of the column.

20 Claims, 2 Drawing Sheets

(56) References Cited

U.S. PATENT DOCUMENTS

| | | | |
|---|---|---|---|
| 6,551,465 | B1 | 4/2003 | Van Zile et al. |
| 6,558,515 | B1 | 5/2003 | Steacy |
| 6,645,350 | B1 | 11/2003 | Steacy |
| 7,090,748 | B2 | 8/2006 | Kaibel et al. |
| 7,264,696 | B2 | 9/2007 | Kaibel et al. |
| 7,267,746 | B1 * | 9/2007 | Harris .................... B01D 3/141 196/111 |
| 7,287,747 | B2 | 10/2007 | Zich et al. |
| 7,357,378 | B2 | 4/2008 | Zone et al. |
| 7,422,197 | B2 | 9/2008 | Zone et al. |
| 7,498,471 | B2 | 3/2009 | Schultz et al. |
| 7,528,290 | B2 | 5/2009 | Zimmermann et al. |
| 7,556,717 | B2 | 7/2009 | Heida |
| 7,604,222 | B2 | 10/2009 | Zone et al. |
| 8,092,655 | B2 | 1/2012 | Burst et al. |
| 8,480,860 | B2 | 7/2013 | Kovak |
| 9,504,934 | B2 | 11/2016 | Agrawal et al. |
| 2014/0231238 | A1 | 8/2014 | Bhargava et al. |

OTHER PUBLICATIONS

EP1681094A2_ENG (Espacenet nnachne translation of Staeck) (Year: 2006).*

Tututi-Avila, S., Dominguez-Diaz, L. A., Medina-Herrera, N., Jimenez-Gutierrez, A., & Hahn, J. (2017). Dividing-wall columns: design and control of a kaibel and a satellite distillation column for BTX separation. Chemical Engineering and Processing: Process Intensification, 114, 1-15. (Year: 2017).*

Tututi-Avila et al., "Dividing-Wall Columns: Design and Control of a Kaibel and a Satellite Distillation column for BTX Separation", Chemical Engineering and Processing, Apr. 1, 2017, vol. 114, pp. 1-15.

The International Search Report and Written Opinion of PCT/US2019/047149 dated Nov. 19, 2019.

* cited by examiner

ADVANCED PROCESS CONTROL SCHEME FOR DIVIDING WALL COLUMN AND DUAL-DIVIDING WALL COLUMN WITH MULTIPLE PRODUCTS

CROSS REFERENCE TO RELATED APPLICATION

This application claims priority to U.S. Provisional Application Ser. No. 62/731,296 filed Sep. 14, 2018, which is herein incorporated by reference in its entirety.

FIELD

Systems and methods are provided for performing separations using distillation columns with having a plurality of dividing walls. The systems and methods include process control schemes.

BACKGROUND

Distillation columns or towers are one of the commonly found structures in a refinery setting. Distillation columns are used for separation of multiple product streams from an input stream using a reduced or minimized amount of footprint in the refinery. Additionally, distillation columns can be valuable for separation of products having adjacent, nearby, and/or overlapping boiling ranges.

Dividing Wall Columns (DWC) are distillation columns containing vertical dividing walls that partition a feed zone from one or more side product drawoff zones. DWC technology allows for reductions in the amount of equipment needed and/or the amount of energy required for performing one or more desired separations. The dividing walls can be used to separate the volume used for receiving input feed(s) to the column from the locations for withdrawal of product streams, thereby reducing product contamination. Additionally or alternately, the dividing walls can be used to create separate compartments for withdrawal of multiple product streams with high purity greater than 99 wt %.

Although dividing wall columns (DWCs) can provide advantages for reduced energy consumption and/or refinery footprint, difficulties remain in implementing dividing wall column technology when a plurality of dividing walls are present within a single column structure. As a practical matter, operating DWCs in a refinery or chemical plant setting requires the ability to primarily control the operation of the column using process control technology. Process control technology typically involves operating the process in region of operating phase space where the controlled variables have responses that can be reasonably approximated as linear responses to moves in the manipulated variables. For many types of processes, process control technology can be implemented in a relatively straightforward manner. However, using process control technology to maintain DWCs with multiple dividing walls in a stable operating region remains a challenge. While increased amounts of operator intervention could be used, it would be preferable to identify systems and methods to allow for improved operation of DWCs using process control technology.

U.S. Pat. No. 6,551,465 describes a dividing wall column control system. In the control system, the rate of return of overhead liquid to the column is set by monitoring the temperature in the top of the product dividing wall section. A sidecut product draw rate is set by monitoring a temperature in the bottom of the product dividing wall section.

SUMMARY

In various aspects, methods are provided for separating a feed into a plurality of products. The methods can include passing a feed comprising i) 1 vol % or more of one or more light components, ii) 1 vol % or more of one or more heavy components, or iii) a combination of i) and ii), into a feed entry volume defined by a first dividing wall and a second dividing wall in a distillation column. The feed entry volume can be in fluid communication with a top common volume and in fluid communication with a bottom common volume. During the passing, a bottom feed entry temperature within the feed entry volume can be maintained between a first temperature and a second temperature. The bottom feed entry temperature can be measured, for example, at a location at least two theoretical stages above a feed vapor split. The first temperature and the second temperature can be greater than a final boiling point of the one or more light components. Additionally or alternately, during the passing a top feed entry temperature within the feed entry volume can be maintained between a third temperature and a fourth temperature. The top feed entry temperature can be measured, for example, at a location at least two theoretical stages below a feed liquid split. The third temperature and the fourth temperature can be less than an initial boiling point of the one or more heavy components. Product streams can then be withdrawn from various divided volumes within the distillation column. In the product streams, a first product stream can include at least a portion of the one or more light components, while another produt stream from a divided volume can include at least a portion of the one or more heavy components. Additionally, a bottom product stream and a top product stream can be withdrawn from the bottom common volume and the top common volume, respectively. During the passing, a concentration of the one or more light components at the feed vapor split can be less than 0.1 vol % and/or a concentration of the one or more heavy components at the feed liquid split can be less than 0.1 vol %.

In various aspects, systems for performing such a separation can also be provided.

DETAILED DESCRIPTION

I. Overview

In various aspects, systems and methods are provided for improving process control of separation systems that include one or more dividing walls within a single column. It has been discovered that improved process control can be achieved by controlling the dividing wall columns based on energy balance instead of mass balance. The energy balancing can be performed in part based on controlling temperature at a plurality of locations on the feed side within a first divided portion of the column. Using energy balancing based on temperature control at a plurality of locations on the feed side can facilitate maintaining the operation of the dividing wall columns within a single region of phase space that can be suitably approximated by linear models. This can allow conventional process controllers to manage the manipulated and controlled variables. In addition to controlling the temperature at a plurality of locations on the feed side, a plurality of other characteristics can be used as manipulated or controlled variables.

One of the difficulties with conventional methods of process control for dividing wall columns to produce four or more products is maintaining the operation of the DWC in a single region of phase space. Using conventional methods for mass balance control of a distillation column, the goal of column operation can be to operate the column to achieve expected amounts of output at each product location. However, in a divided wall column, different temperatures can be present on opposing sides of a dividing wall. As a result, attempting to manage a column containing a dividing wall based on a mass balance of the feed versus the products can result in unpredictable behavior. For example, in a conventional distillation column, if too much of the feed is being fractionated into an intermediate product, the conventional mass balance response can be to reduce the temperature. However, this may not produce the desired outcome in a column with a dividing wall. In a column with a feed entry volume that is separated from intermediate products by a dividing wall, a potential reason for excess product at a product withdrawal location is due to improper separation of the feed in the feed entry volume. In particular, the initial portion of the column that receives the feed (i.e., the feed entry volume) is typically expected to divide the feed based on boiling range, with certain light components being expected to exit above the liquid split and certain heavy components expected to exit below the liquid split. If the light components exit below the liquid split, excess product can be present at a product withdrawal location. However, attempting to cool the product location will not resolve this issue, and in fact could cause it to become worse by causing a corresponding decrease in temperatures in the feed entry volume on the opposing side of the dividing wall. A similar problem can arise when heavy components exit above the liquid split. Thus, in a mass balanced based control approach, there is a potential that the column could enter a region of phase space where attempting to "correct" the amount of product at an intermediate location could result in taking the column further from the desired operating region.

It has been discovered that control of DWCs can be improved by maintaining energy balance within the column. Instead of attempting to balance the output product draws with the amount of input feed, a DWC can instead be controlled based on maintaining desired or target temperatures at various locations within the DWC. In particular, temperatures near the top and bottom of the feed entry volume can be controlled in order to prevent light components from exiting below the vapor split and prevent heavy components from exiting above the liquid split. By controlling temperatures in the column to achieve target values and target product purities, the operation of the column can be maintained in a desired region of phase space. Optionally, one or more of the target temperatures and/or temperatures used for controlling a controller can correspond to pressure-compensated temperatures, in order to account for the impact of pressure on volatility of components within the column.

As an example, a feed could contain 1 vol % or more of one or more light components (or 10 vol % or more), and/or 1 vol % or more of one or more heavy components (or 10 vol % or more). The one or more light components, if present, correspond to components that are part of an intermediate product from the tower (i.e., not part of the top product from the tower). Similarly, the one or more heavy components, if present, correspond to components that are part of a different intermediate product from the tower. In various aspects, when operating the column, the one or more light components can be prevented from exiting the feed entry volume via the vapor split at the bottom of the dividing wall defining the feed entry volume. Additionally or alternately, the one or more heavy components can be prevented from exiting the feed entry volume via the liquid split at the top of the dividing wall defining the feed entry volume. This can correspond to, for example, limiting the amount of the one or more light components at the vapor split to 0.1 vol % or less of the composition at the vapor split. Similarly, the amount of the one or more heavy components can be limited to 0.1 vol % or less of the composition at the liquid split.

In order to control the plurality of temperatures in the feed entry volume, other variables that can be manipulated and/or controlled include (but are not limited to) the tower overhead pressure, the reboiler or heater duty, the cut-point temperature for one or more of the product draws, the draw rate for one or more of the product draws, the feed flow rate, the bottoms flow rate, the overhead internal reflux, the overhead distillate, the bottoms level, and the reflux drum level. Additionally, the feed and/or product compositions can be analyzed as a further source of input. For example, control of the reboiler duty and the overhead internal reflux can allow for control of temperature at various locations within the column, including within the feed entry volume.

In addition to using energy balancing, at least a portion of the manipulated and the controlled variables can be related to each other by use of a multivariable controller. A multivariable controller can allow a variety of input values to be selected from when determining how to perform energy balancing. For example, rather than selecting a reboiler duty based on a bottoms temperature, it may be desirable to set the reboiler duty based on a temperature within the feed entry volume. In order to control a temperature at both the top and bottom of the feed entry volume, the amount of internal reflux at one or more locations can be controlled by the multivariable controller as well. One difficulty with operators operating a column using an energy balance control scheme is that an increased amount of energy is typically used. By using a multivariable controller for management of a plurality of variables, the amount of energy required to operate the column based on energy balance can be reduced or minimized.

II. General Dividing Wall Column Configuration and Operation

In order to facilitate illustration of the control scheme for a dividing wall column, a brief description of a general dividing wall column configuration is provided.

In various aspects, configurations and/or methods as described herein can be used to allow for production of 5 or more products (or 4 or more products, or 6 or more products) from a dividing wall column containing a plurality of dividing walls. Optionally, such configurations can include a maximum of two vapor splits and two liquid splits. Reducing or minimizing the number of vapor splits and/or liquid splits in a dividing wall column configuration can be beneficial as each split corresponds to a location where flows have to be managed so that the pressure is equalized at the split point. Therefore, reducing or minimizing the number of splits can reduce the number of constraints on the flows within the system and reduce the complexity of the design and operation. It is noted that when counting the number of products, a top product and a bottoms product from the divided wall column can correspond to products that are withdrawn from common packed beds within the dividing wall column. With regard to the bottoms product, it is noted that at least a portion of the bottoms product can typically be recycled as part of a reboiler loop to provide additional heat to the distillation column. Additionally, configurations and/or methods are also provided for columns including a single dividing wall, such as a column for producing 4 products.

In some aspects, generating 5 or more products from a dividing wall column containing two or more dividing walls may require maintaining a temperature differential of at least 10° C. across at least one dividing wall, or at least 20° C., or at least 25° C., such as up to 35° C. or possibly more. Maintaining a temperature differential across at least one dividing wall may allow products with different boiling ranges to be withdrawn at a similar height or elevation in the column while still achieving a desired purity.

In some aspects, generating 5 or more products from a dividing wall column can be facilitated by having different packing types and sizes on opposite sides of a dividing wall. Use of different packing types and sizes would be design considerations to optimize the tower design to improve or maximize utilization and reduce or minimize waste volume. As a result of using different packing types and sizes, the pressure drop, capacity and packing efficiency for each horizontally adjacent packed bed section may vary. This can potentially cause the ratio of gas mass flow to cross-sectional area to vary within various portions of the dividing wall column.

In some aspects, 5 or more products can be generated from a dividing wall column while operating the column at a pressure of 100 kPa or more, or 150 kPa or more, while still having a maximum of 2 liquid splits and 2 vapor splits. Operating a column at higher pressure can sometimes be beneficial.

It has been discovered that during operation of a distillation column, it can be desirable to have substantially equal flood percentages for packed beds in divided volumes where side drawoff products are withdrawn. When operating a distillation column with substantially equal flood percentages, a target flood percentage can be identified that is within a threshold amount of the flood percentages for any packed beds in divided volumes wherein side drawoff products are withdrawn. It is noted that in some aspects, trays could be used as an alternative to packed beds within a dividing wall column. In order to simplify this description, packed beds are described herein to illustrate the invention.

In some aspects, the distillation column can be designed to have a roughly equal average percent flood in each divided (i.e., adjacent) section of a packed bed. The divided sections are separated from each other by the dividing wall(s). Designing for approximately equal percent flood for each divided section is expected to maintain constant vapor flow split and maximize the overall hydraulic capacity of the column to handle an increase in feed flow, as each of the packed beds in the divided volumes has a similar amount of remaining capacity. This may allow the use of different packing types and sizes for each tower section depending on the separation requirements. Additionally or alternately, operating with roughly equal percent flood can allow for flexibility in processing feeds with varying compositions, as the pressure drop across the packed beds can have a reduced or minimized variability as the amount of compounds in a particular boiling range changes between feeds. This is in contrast to attempting to operate the distillation based on control of the gas flows within one or more of the divided volumes defined by the dividing walls which may constrain the packing selection to similar packing type and size for the horizontally adjacent packed beds. In this discussion, operating with roughly equal average percent vapor flood in adjacent packed beds is defined as operating with average percent vapor flood values that differ by less than 10%. One potential benefit of operating with roughly equal average percent vapor flood values is that this can allow a dividing wall column to maintain substantially similar vapor split ratios when operating at substantially different feed rates to the column. A substantially different feed rate is defined as having a first feed rate that differs from a second feed rate by 25% or more. A substantially similar vapor split ratio is defined as having a first vapor split ratio that differs from a second vapor split ratio, for the same vapor split, by less than 10%.

In some aspects involving configurations for generating at least four products from a dividing wall column, at least one of the dividing walls can correspond to a plurality of dividing wall sections, with at least one dividing wall section being horizontally offset or staggered relative to at least another dividing wall section. Having an offset wall section can change the relative cross-section of the divided volume(s)/tower sections defined by the plurality of wall segments. This can assist with maintaining a constant flood volume percentage across various packed beds by modifying the total volume available for flooding within a given packed bed. Additionally or alternately, using an offset wall configuration can provide an increased amount of usable packed bed volume within a distillation column relative to a configuration that involves a single, contiguous dividing wall with an angled section. For example, the stagger or offset location for a stagger wall can occur within a column internal component, such as within a chimney tray. Having the stagger location occur within a column internal can reduce or minimize any potential impact of the wall stagger on the fluid flow within the column. A stagger location within a column internal can also reduce or minimize the amount of volume that is not occupied by a packed bed. A dividing wall column (DWC) with an angled dividing wall may result in a design with more waste volume than a DWC using staggered dividing walls. For example, DWC configurations that employ a sloped or angled dividing wall typically do not have a packed bed adjacent to the sloped portion of the dividing wall. This can result in leaving a substantial portion of the column volume empty.

In some aspects, the plurality of dividing walls can allow multiple products to be withdrawn from various divided volumes while reducing or minimizing the height of the packed bed(s) between the multiple products. In a conventional distillation column, the products withdrawn from adjacent heights in the column typically correspond to products with overlapping or adjacent boiling ranges. By creating divided volumes for withdrawal of side drawoff products, products with higher purity can be withdrawn from distinct divided volumes. For example, a distillation column including two dividing walls can have a feed entry volume and a plurality of divided volumes separated from the central volume for withdrawal of products. If three side drawoff products are desired in addition to the top and bottom product, two of the three side drawoff products can be withdrawn from divided volumes defined in part by a first dividing wall (corresponding to a first tower section) the remaining side drawoff product can be withdrawn from a divided volume defined in part by a second dividing wall (corresponding to a second tower section). In such aspects, the withdrawal locations can be configured so that the boiling range of the side drawoff product withdrawn from the second tower section can correspond to a boiling range between the products withdrawn from the second tower section. This configuration can reduce or minimize the number of equivalent trays needs to achieve a desirable separation between products. This configuration is expected to reduce the height of the packed bed(s) located between the two side drawoff product withdrawal locations in the first tower section. For example, instead of the typical requirement of at least 10 equivalent trays for suitable separation of products, the packed bed between the product withdrawal locations in the first tower section can correspond to 5 equivalent trays or less depending on the change in relative volatility between the vertically adjacent side products.

Operating with roughly constant percent flood in the divided volumes can be in contrast to conventional strategies for operating a dividing wall column. Examples of conventional strategies for dividing wall column operation include operating at constant ratio of gas mass flow to cross sectional area in the divided volumes, which may not fully utilize tower capacity, efficiency, or allow for different types of packings and sizes for each divided section.

III. Definitions

In this discussion, a dividing wall is defined as a partition wall or other barrier that prevents fluid flow that is disposed roughly parallel to/passes through the central axis of a distillation column. The dividing wall can intersect with the interior wall of the distillation column (referred to as the column wall) in one or more locations, such as intersecting in two locations. The dividing wall can typically have a height that is less than the interior height of the distillation column.

In this discussion, a divided volume is defined as a volume within a distillation column that is bounded laterally by at least one dividing wall and either the column wall or a second dividing wall. This is in contrast to a common volume within a distillation column, which refers to a volume that spans substantially the entire interior cross-section of the distillation column at the heights/elevations corresponding to the common volume. Divided volumes have substantially no fluid communication laterally through a dividing wall. Instead, any fluid communication between divided volumes that are separated by a dividing wall is indirect, based on fluid communication via, for example, an upper common volume or a lower common volume. The vertical boundaries for a divided volume are based on the packed beds and other associated internals in the dividing wall column. In this discussion, the vertical boundaries of a divided volume are defined as the top of the liquid distributor tray(s) (or other flow distributor) located above a packed bed to the bottom of the chimney tray, liquid withdrawal tray, or another structure suitable for product withdrawal below the same packed bed. If a liquid/flow distributor is not present above a packed bed, then the divided volume starts at the top of the packed bed. If a chimney tray or other comparable structure is not present below a packed bed, then the divided volume ends at the structure that starts the next divided volume. It is noted that the divided volumes in a dividing wall column do not need to be contiguous under these definitions. It is further noted that the feed entry volume may not correspond to a divided volume. For example, the feed entry volume may correspond to a volume between a chimney tray and a flow distributor. Finally, it is noted that a packed bed and associated internals may not correspond to a divided volume under this definition if a portion of the associated internals are beyond the dividing wall. For example, two sections of adjacent packed beds may be separated by a dividing wall, but may share a common chimney tray that is below the level of the dividing wall. This type of internal configuration falls outside of the definition of a divided volume.

In this discussion, a tower section corresponds to a portion of the tower that is defined in part by a lateral boundary formed by a dividing wall, with a top and bottom defined by the top and bottom of the corresponding dividing wall. For a section that is bound on multiple sides by a dividing wall, the lowest elevation top and the highest elevation bottom can be used to define the section. A tower section can include one or more divided volumes.

In this discussion, a liquid split is defined as a location corresponding to a top of a dividing wall where two horizontally adjacent packed beds are divided and the liquid flow rates to the top of these beds are manipulated to achieve the desired component separation in each packed bed. In this discussion, a vapor split is defined as a location corresponding to a bottom of a dividing wall where two horizontally adjacent packed beds are divided and the vapor ratio to each side of the dividing wall is set by the design of the column internals.

In this discussion, a packed bed is defined according to the conventional definition. Therefore, a packed bed has an available volume between the particles/structures and/or in the pores in the packed bed for holding a fluid. References to a total volume for a packed bed correspond to this available volume. In this discussion, percent vapor flood for a packed bed is defined as the percent capacity relative to the flood point, which is defined by Fractionation Research, Inc. (FRI). In this discussion, a target percent flood corresponds to a value for comparison with the percent flood for packed beds within the divided volumes in a distillation column.

In this discussion, side drawoff products refer to distillation products other than products withdrawn from the top common volume or the bottom common volume.

In this discussion, references to boiling points or distillation points correspond to distillation points as determined according to ASTM D2887, or alternatively according to ASTM D86 and/or ASTM D7169 if ASTM D2887 is unsuitable due to the nature of the sample. References to "Tx" distillation points refer to a fractional weight "x" of a sample that can be distilled at the identified temperature. For example, a T10 distillation point corresponds to a temperature at which 10 wt % of a sample can be distilled. In this discussion, boiling points and/or ranges for fractions that include compounds corresponding to light ends (i.e., $C_1$ to $C_4$ compounds) may be described based on the carbon number of the hydrocarbons that are included within a fraction, in accordance with the common practice by those of skill in the art. For example, a boiling range that is described as $C_4$ to 200° C. represents a boiling range that has a sufficiently low endpoint to include $C_4$ hydrocarbons. Similarly, a light ends fraction corresponding to $C_1$ to $C_4$ compounds can have a boiling range with a sufficiently low endpoint to include methane and a sufficiently high endpoint to include $C_4$ hydrocarbons.

In this discussion, two product streams can be compared based on the volatility of the streams as determined by normal boiling point. In this discussion, comparing the volatility of two streams based on normal boiling point is defined as comparing the streams based on the T50 boiling points of the streams at normal conditions (i.e., 1 atm or ~100 kPa-a). A first stream is defined as having lower volatility than the second stream if the T50 boiling point of the first stream is higher than the corresponding T50 boiling point of the second stream.

In this discussion, fluid communication can refer to direct fluid communication or indirect fluid communication. Indirect fluid communication refers to the ability for fluids to pass from a first volume to a second volume via an intervening volume.

In this discussion, the term substantially parallel refers to a wall/wall section that is oriented to within 10° or less of being parallel to an axis or another wall/wall section.

In this discussion, opposing locations for a dividing wall are defined as locations adjacent to a dividing wall at a given location that are on opposite sides of the dividing wall.

IV. Base Control Scheme

In various aspects, a base control scheme can be used for control of a distillation column including one or more dividing walls, such as a dual dividing wall column (DDWC) or a column having multiple dividing walls (MDWC). The base control scheme will look different for different tower services depending on the feed compositions, the sizes of the product streams, and the availability of lights for pressure control. However, such base control schemes can be based on various control principles. The control principles can include, but are not limited to, control over temperatures in the feed entry volume; control of overhead internal reflux; control of product purity; control of reboiler heat duty; and control of the column or tower bottoms level. In some aspects, managing this plurality of control principles can be facilitated by use of a multivariable controller. In addition to simplifying management, it has been discovered that a multivariable controller can reduce the energy requirements for operating a column including one or more dividing walls, such as two dividing walls or a plurality of dividing walls.

The base control scheme for a DWC can be based on process controllers, such as proportional-integral-derivative controllers, or another convenient type of controller. Such controllers can typically receive a single input, which is then used to determine a single output signal. Such base A common element in the base control for a DWC regardless of the nature of the feed is stable separation control in the feed entry volume (i.e., on the feed side of a dividing wall). This control prevents the light key components from slipping under the wall and the heavy key components from spilling over the wall. Doing this successfully for 100% of the time can facilitate the success of a model-based multivariable controller on top of this base control scheme.

In various aspects, maintaining a steady separation in the feed entry volume can be based on an energy balance control scheme. Material balance control schemes typically do not perform sufficiently well.

A. Feed Entry Volume Separation Control

Maintaining sufficient control over the separation in the feed entry volume is starting point for operation of a base control scheme. This can correspond to maintaining temperature control for at least two locations within a feed entry volume. One location corresponds to a location at least two theoretical stages below the liquid split (i.e., the top of the wall), such as two to five stages below the liquid split. This can be referred to as a top feed entry temperature. A second location corresponds to a location at least two theoretical stages above the vapor split, such as two to five stages above the vapor split. This can be referred to as a bottom feed entry temperature.

A variety of control options are possible for controlling both the top feed entry temperature and the bottom feed entry temperature. For example, in some aspects the top feed entry temperature can be influenced and/or stabilized by the overhead product quality control, the upper side stream product quality control, or a combination thereof. In such aspects, there may be no base control scheme to control the top feed entry temperature. Instead, the model-based multivariable controller can manage one or more controls to maintain a desired top feed entry temperature. Alternatively, the top feed temperature may be incorporated into the base control scheme by using the top feed temperature as one of the constraints for the reboiler duty control.

An example of a control option for control of the bottom feed entry temperature can be based on control of the internal reflux to the feed side of the wall defining the feed entry volume. A feed reflux draw can be withdrawn above the liquid split that defines the feed entry volume. A feed reflux splitter can then be used to control the amount of reflux liquid that is returned to a location above the feed entry volume versus liquid that is returned above the opposite side of the dividing wall. This can provide control over the amount of cooling that takes place in the feed entry volume. Depending on the aspect, this can be used to facilitate control of the top feed entry temperature and/or the bottom feed entry temperature.

In some aspects, the reflux flow to the feed entry volume from the reflux splitter can be monitored by a suitable method, such as by using a full-bore ultrasonic flow meter. In such aspects, the flow meter can include at least three pick-ups for determining the flow rate. Due to the frothy nature of the potentially near boiling flow in the reflux line, having fewer pick-ups and/or a different type of flow meter can potentially lead to inaccurate flow measurements.

B. Product Purity Control

In a dividing wall column, such as a dual dividing wall column, a plurality of products can be generated by the column. The purity of one or more of the products (and optionally the purity of each of the products) can be controlled in part based on a draw rate at the product location, the internal reflux below the product withdrawal location, and/or information regarding changes in the incoming feed to the feed entry volume.

In various aspects, the internal reflux to the feed side of the wall can be calculated. Usually this will be equal to the measured external reflux flow to the feed side of the wall. Optionally, if the reflux flow (such as the reflux flow to the product side of the wall) is heated by the pumping used to provide pressure for the reflux, a temperature sensor can be used to calculate the reduction of the internal reflux due to the heating. An internal reflux flow controller, for the portion of the feed reflux that is returned above the feed side of the wall, can reset the position of the reflux splitter (i.e., can determine the amount of reflux delivered above the feed entry volume). The setpoint for the internal reflux flow controller can be reset, for example, based on determining a pressure-compensated value for the bottom feed entry temperature.

In aspects where product purity is controlled in part based on reflux below the product withdrawal location, an internal reflux below the product draw tray can be calculated. This can be determined, for example, by deducting the draw rate from the internal reflux above the draw tray. For a product draw tray located in a wall section (i.e., in a divided volume), the internal reflux to the product draw side of the wall can be calculated first in order to determine the reflux in just the divided volume associated with the product draw.

After calculating the internal reflux below the draw tray, the internal reflux flow below the draw tray can be used as process variable to a controller that controls the internal reflux below the draw tray. This controller can reset the draw rate controller to control the product draw. With regard to a setpoint for the internal reflux below the draw tray, a pressure-compensated temperature controller for the cut point relevant for the product quality of the draw can be used to reset the setpoint of the internal reflux below the draw tray controller.

In some aspects, a dividing wall column can have a significant draw rate for products near the middle of the tower. But for higher or lower side stream products in some aspects, the draw rate may provide insufficient control authority for tight internal reflux below the draw tray control. In other words, the draw rate may not have a sufficient impact on the temperature to provide a desired level of temperature control. In such aspects, a multivariable controller can optionally manipulate the draw rate rather than a base control temperature setpoint. This can be beneficial for avoiding situations where model prediction errors are introduced into the multivariable controller due to a lack of ability of the base control to maintain temperature at or near a product withdrawal location.

In addition to the above, in some aspects it can be beneficial for the base control scheme to use feed information when determining a product draw amount. For example, when significant and sudden changes in feed rate and feed composition occur, it can be beneficial to provide a dynamically compensated material balance feed forward control to the affected product draw while in base control. It is noted that this can preferably be bypassed when the multivariable model based control is being used to control product quality, rather than the base control.

C. Overhead Control

In various aspects, it is beneficial for the pressure within the column to be stable in all circumstances, including rainstorms that create internal reflux fluctuations. Because the overall control uses energy balance control, pressure disturbances may cause the complete control scheme to cycle.

In some aspects, an initial step for overhead control can be to calculate and control the tower internal reflux using the overhead temperature, external reflux flow, and the reflux temperature. The overhead draw stream composition can be controlled by a temperature controller resetting the internal reflux control.

The additional details for pressure control can be dependent on the nature of the components in the overhead section. For example, some overhead sections can include a flooded, drum-less overhead condenser. In some aspects, the overhead draw rate may be large enough to allow for sufficient overhead pressure control authority. In such aspects, a) a reflux ratio control valve can used to control internal reflux; b) a pressure-compensated tray temperature controller for overhead product quality control can reset the setpoint of the internal ratio controller; and c) a tower overhead pressure controller can reset the setpoint of the overhead product draw. Optionally, adding the external reflux flow as feed forward to the pressure control can further improve pressure control stability.

In other aspects, the overhead draw may not provide sufficient control authority for overhead pressure control. In such aspects, a) the reflux control valve can be used to control internal reflux; and b) the tower overhead pressure controller can reset the internal reflux ratio controller setpoint. Since the overhead draw is a small flow, the feed forward to the pressure control has limited justification. Additionally, the pressure compensated tray temperature controller for overhead product quality control can reset the setpoint of the overhead product draw. This control scheme is less performant for product quality control in the top, but it can be beneficial for maintaining constant pressure in the tower.

In still other aspects, the overhead components can include a partial overhead condenser with a small vapor product stream and reflux drum. In such aspects, pressure control can be achieved by manipulating the small vapor product stream flow rate. If the overhead liquid draw rate is large enough for sufficient reflux drum level control authority, a) the reflux control valve is used to control internal reflux; b) the pressure compensated tray temperature controller for overhead product quality control can manipulate the setpoint of the internal reflux ratio controller; and c) the reflux drum level controller can reset the overhead liquid product flow rate controller. Alternatively, if the overhead draw does not provide sufficient control authority for reflux drum level control, level control can be handled as part of the model-based, multivariable controller. In such alternative aspects, the multivariable controller can manipulate the internal reflux (which manipulates the flow of external reflux) and overhead liquid product. Additionally, the internal reflux ratio controller can be manipulated by a back-up drum level controller if the model-based, multivariable controller is not on.

D. Reboiler Heat Duty Control

Reboiler heat duty is calculated as a process variable, and it is used in a heat duty controller to manipulate the ultimate handle that manipulates the heating medium to the reboiler.

The reboiler heat duty can be manipulated by the model-based, multivariable controller to handle varying constraints in the dividing wall column. When this controller is not available, the reboiler heat duty setpoint can be manipulated by the pressure compensated tray temperature controller relevant to the bottom product quality. However, in a dividing wall column, the bottom product quality control may not be the constraining control for heat demand. In that case, an overriding controller may be required to provide sufficient heat for adequate fractionation higher up in the column. Alternatively, in aspects where a multivariable controller is not used, a pressure-compensated temperature controller higher up in the column can reset the heat duty setpoint.

E. Tower Bottoms Level Control

Typically the bottoms draw rate controller setpoint can be reset by the tower bottoms level controller. In cases where the multivariable, model-based controller links towers together, the bottoms flow can be manipulated by it directly. A multivariable controller can also be beneficial in instances where a feed contains a reduced or minimized amount of bottoms material.

F. Multivariable Model Based Control for a Divided Wall Column

In various aspects, a multivariable controller can be used to coordinate control of a plurality of variables within a divided wall column. Using a multivariable controller can provide a way for information and/or control structures from disparate portions of a column to interact, as well as allowing multiple variables to be considered and/or selected from when selecting a setpoint for variables such as the reboiler heat duty cycle.

In some aspects, a multivariable model based controller can be configured to interact with a plurality of manipulated (independent) variables, a plurality of controlled (dependent) variables, and optionally one or more independent feed forward or disturbance variables.

As an example, the manipulated variables can include, but are not limited to, tower overhead pressure; reboiler heat duty; setpoint of bottom feed entry temperature control; setpoint of one or more of the base control cut-point temperature controllers for products (such as setpoint for all of the cut-point temperature controllers); draw rate for products where base control tray temperature control would not be successful; feed flow rate (this may alternatively be a feed-forward/disturbance variable); bottoms flow rate (if bottoms level is included in the multivariable, model-based controller); and overhead internal reflux and overhead distillate (such as in aspects where the tower includes a reflux drum).

The feed-forward or disturbance variables can include, but are not limited to, tower feed composition based on output from a feed analyzer, such as a gas chromatograph; and tower feed rate (if not manipulated by the multivariable, model-based controller).

The controlled variables can include, but are not limited to, top feed entry temperature; product draw compositions, based on analyzers; sensitive tray temperatures where no base control tray temperature was built; bottoms level (if included); reflux drum level (if reflux drum exists) or overhead condenser level; tower delta pressure as a flooding constraint; and various additional tower constraints, such as controller outputs and/or valve positions.

It is noted that the limits on the variables for the top feed entry temperature and bottom feed entry temperature are important for ensuring that light key components cannot slip under the wall defining the feed entry volume and/or heavy key components cannot spill over the wall defining the feed entry volume. It is also noted that reboiler heat duty is not necessarily linked to the bottoms separation, but also impacts many of the multivariable dependent variables.

Depending on the aspect, a multivariable controller can be used to facilitate manipulation and/or control for groups or pluralities of variables that would normally not be considered as interacting under base control methodology. The model for operation of the multivariable controller can be formed based on the manipulated, disturbance, and controlled variables that are considered desirable for allowing interaction. As an example, the reboiler heat duty (manipulated variable) can be set based on consideration of temperature input from a large plurality of temperatures throughout the column. Additionally, variations in the feed detected by a feed analyzer can also be considered when selecting the reboiler heat duty. Based on such changes to the reboiler heat duty, a multivariable controller can also modify setpoints related to one or more reflux splitters, to maintain one or more temperatures at target values even though additional heat is being added to the bottom of the column. More generally, any desired combination of manipulated variables, disturbance variables, and controlled variables can be incorporated into the model for the multivariable controller, to allow for management of a dividing wall column as described herein.

The base control scheme in itself stabilizes the separation. It is designed such that the complete DWC will seem like a classic distillation column with linear behavior to a multivariable controller. But the base control typically cannot run a DWC efficiently, because of the many interactions. In various aspects, a multivariable model-based control can be used to control the heat input and product compositions to meet specifications while being energy efficient. Properly designed base control with the right design of multivariable control can be beneficial for successful and efficient operation of a DWC.

In various aspects, a multivariable controller can be referred to as being in receiving communication with one or more sensors and/or controllers within a dividing wall column. Receiving communication is defined as being able to receive signal communication from the sensor and/or controller. Additionally, a multivariable controller can be in input communication with one or more controllers for providing input regarding the setpoint for the controller.

G. Instrumentation

In order to provide information regarding temperatures, pressures, compositions, flow rates, and/or other values within a dividing wall column, a variety of instrumentation can be used. Examples of instrumentation can include, but are not limited to, a) a feed analyzer for feed forward control on product draw trays and heat input; b) impurities analyzers associated with one or more product streams (such as potentially all product streams) for product quality control; c) composition analyzers for reflux flows from reflux splitters; d) overhead pressure sensor(s); e) overhead temperature sensor(s); f) reflux temperature sensor(s); g) a level indicator for the overhead drum (if present); h) a level indicator for the tower bottoms and additional level indicators including level indicator 1465 at other locations in the tower; i) instrumentation to allow for calculation of the heat input from the reboiler (such as using flow and temperature measurements to determine a heat input from the reboiler in MW or another power unit); j) a full-bore ultrasonic flow meter with a plurality of pick-ups for the reflux flow to the feed entry volume, and k) temperature sensors and optionally pressure sensors including pressure indicator 1493 for cut-point control at sensitive temperature locations. This can include temperature detection for temperatures such as the top feed entry temperature and the bottom feed entry temperature. Additionally or alternately, one or more temperature sensors can be associated with each product cut, such as three per product cut, as part of product purity control. For products that can tolerate higher levels of impurities, such as impurity levels of 5 vol % or more, a single thermocouple may be sufficient. Optionally, the temperature sensors can also be associated with pressure sensors, to allow for calculation of pressure-sensitive temperature values.

V. Variations in Packed Beds on Opposing Sides of Dividing Walls

Conventionally, managing the flows on either side of a dividing wall column has been managed by limiting the nature and types of differences on the opposing sides of a dividing wall. As an example, conventional dividing wall columns have used the same type of packed bed throughout a column. By using the same type of packing material, and by having packed beds of matching depths on either side of dividing walls, the pressure drops on either side of a dividing wall can be similar and therefore the amount of fluid flow in the volumes defined by the dividing wall can be relatively predictable.

In contrast to conventional configurations, in various aspects dividing wall columns can be used that allow for divergent fluid properties on opposing sides of a dividing wall for at least some locations. Structurally, the variations in fluid properties can be achieved by including structures with different pressure drops on opposing sides of a dividing wall. For example, instead of having packed beds of similar packing type, size, and depth on each side of a dividing wall, the packed beds on opposing sides of a dividing wall can be varied. Differences in the packed beds on opposing sides of a dividing wall near the top of the wall can eventually be balanced by other differences toward the bottom of the dividing wall. It is noted that above the top of a dividing wall (or below the bottom of a dividing wall), any pressure differences will be resolved due to the absence of a structure that can maintain a pressure differential.

Another type of variation that can assist with having divergent fluid properties on opposing sides of a dividing wall can correspond to a variation in the cross-sectional area for the divided volumes on opposing sides of a wall while reducing or minimizing the amount of waste volume created in the column. Changing the cross-sectional area can change the relative pressure drop on both sides of a dividing wall. For example, in a tower section having a constant cross-sectional area, if all beds in the tower section have the same packing type, size, and cross-sectional area, the pressure drop across each packed bed can be primarily determined by the depth of the bed. However, if the cross-sectional area of one of the packed beds is larger while keeping the same packing material/packing density/bed depth, the overall pressure drop across such a packed bed can be lower due to the increased area that is available to accommodate the flow.

In some aspects, maintaining a temperature variation on opposing sides of a dividing wall can be facilitated or enhanced by using a dividing wall with increased insulating properties, such as a dividing wall composed of two wall structures separated by a wall gap. The wall gap can correspond to an air gap, a vacuum gap, or another convenient type of gap that can reduce or minimize heat transfer between the wall structures. In aspects where a dividing wall corresponds to a chord between two points on the circumferential inner wall of the column, the wall structures can be separated by the wall gap along the full length of the walls. Any convenient gap size can be used between the separated wall structures, such as a wall gap of 0.3 inches (~0.7 cm) to 3.0 inches (~7.6 cm), or 0.5 inches (~1.2 cm) to 2.0 inches (~5.1 cm).

VI. Feedstocks

Any convenient type of feedstock that is suitable for separation in a traditional distillation column and/or plurality of columns can be separated using a dividing wall column. Examples of suitable feeds for separation can include, but are not limited to, hydrocarbon (or hydrocarbon-like) feeds. Hydrocarbon-like feeds can include feeds that have one or more heteroatoms other than carbon or hydrogen. Examples of hydrocarbon-like compounds include, but are not limited to, oxygenates (such as alcohols, esters, and ethers), nitrogen-containing compounds (such as amines), and sulfur-containing compounds (such as mercaptans). It is noted that such heteroatoms may be contained in a ring structure, such as a cyclic ether or a thiophene.

In some aspects, a suitable feed (or other fraction) can have a boiling range that includes light ends. For example, the lower end of the boiling range can be sufficiently low to include $C_1$ hydrocarbons, or sufficiently low to include $C_2$ hydrocarbons (but exclude $C_1$ hydrocarbons), or sufficiently low to include $C_3$ hydrocarbons (but exclude $C_2$ hydrocarbons), or sufficiently low to include $C_4$ hydrocarbons (but exclude $C_3$ hydrocarbons). For example, a feed (or other fraction) that includes various types of light ends can have a boiling range defined by an initial boiling point to a T90 distillation point of $C_1$ to 350° C., or $C_1$ to 270° C., or $C_1$ to 200° C., or $C_1$ to 150° C. As another example, a feed (or other fraction) that includes $C_2$ hydrocarbons can have a boiling range defined by an initial boiling point to a T90 distillation point of $C_2$ to 350° C., or $C_2$ to 270° C., or $C_2$ to 200° C., or $C_2$ to 150° C. As still another example, a feed (or other fraction) that includes $C_3$ hydrocarbons can have a boiling range defined by an initial boiling point to a T90 distillation point of $C_3$ to 350° C., or $C_3$ to 270° C., or $C_3$ to 200° C., or $C_3$ to 150° C. As yet another example, a feed (or other fraction) that includes $C_4$ hydrocarbons can have a boiling range defined by an initial boiling point to a T90 distillation point of $C_4$ to 350° C., or $C_4$ to 270° C., or $C_4$ to 200° C., or $C_4$ to 150° C. As still another example, a feed (or other fraction) that includes $C_5$ hydrocarbons can have a boiling range defined by an initial boiling point to a T90 distillation point of $C_5$ to 350° C., or $C_5$ to 270° C., or $C_5$ to 200° C., or $C_5$ to 150° C.

In other aspects, a suitable feed can have a T10 distillation point of at least 60° C., or at least 90° C., or at least 120° C. In some aspects, a suitable feed can have a T90 distillation point of 350° C. or less, or 300° C. or less or 270° C. or less, or 200° C. or less, or 150° C. or less. For example, suitable feeds can have a T10/T90 distillation range of at least 60° C. to 150° C. or less, or at least 60° C. to 200° C. or less, or at least 60° C. to 300° C. or less, or at least 90° C. to 200° C. or less, or at least 90° C. to 270° C. or less, or at least 120° C. to 300° C. or less, or at least 120° C. to 350° C. or less. It is noted that feeds with still higher T90 distillation points may be suitable for separation, as such higher boiling portions of a feed can form a "bottoms" fraction while the lower boiling portions correspond to the products withdrawn from various divided volumes.

As an example, a feed composed of primarily benzene, toluene, xylene along with light ends and heavy components as impurities. The corresponding separation could produce at least 5 products, corresponding to a light ends product, a heavy product, and products substantially corresponding to benzene, toluene, and xylene. Such a separation could be performed in a dividing wall column separator having two dividing walls, with the benzene, toluene, and mixed xylene products being withdrawn from different divided volumes in the tower sections defined by a dividing wall and the interior wall of the column.

As another example, a suitable feed can correspond to a feed that includes hydrocarbons (or hydrocarbon-like compounds) containing 6 or more carbons per compound. In such an example, a dividing wall distillation column could be used to form 6 products. A top product could correspond to a $C_9$ or lighter product while a bottoms product could correspond to a $C_{18}$ or heavier product. The divided volumes from one tower section could be used to withdraw a $C_{10}$-$C_{11}$ product and a $C_{14}$-$C_{15}$ product, while divided volumes from a second tower section could be used to withdraw a $C_{12}$-$C_{13}$ product and a $C_{16}$-$C_{17}$ product.

VII. Configuration Example

Figure 1:
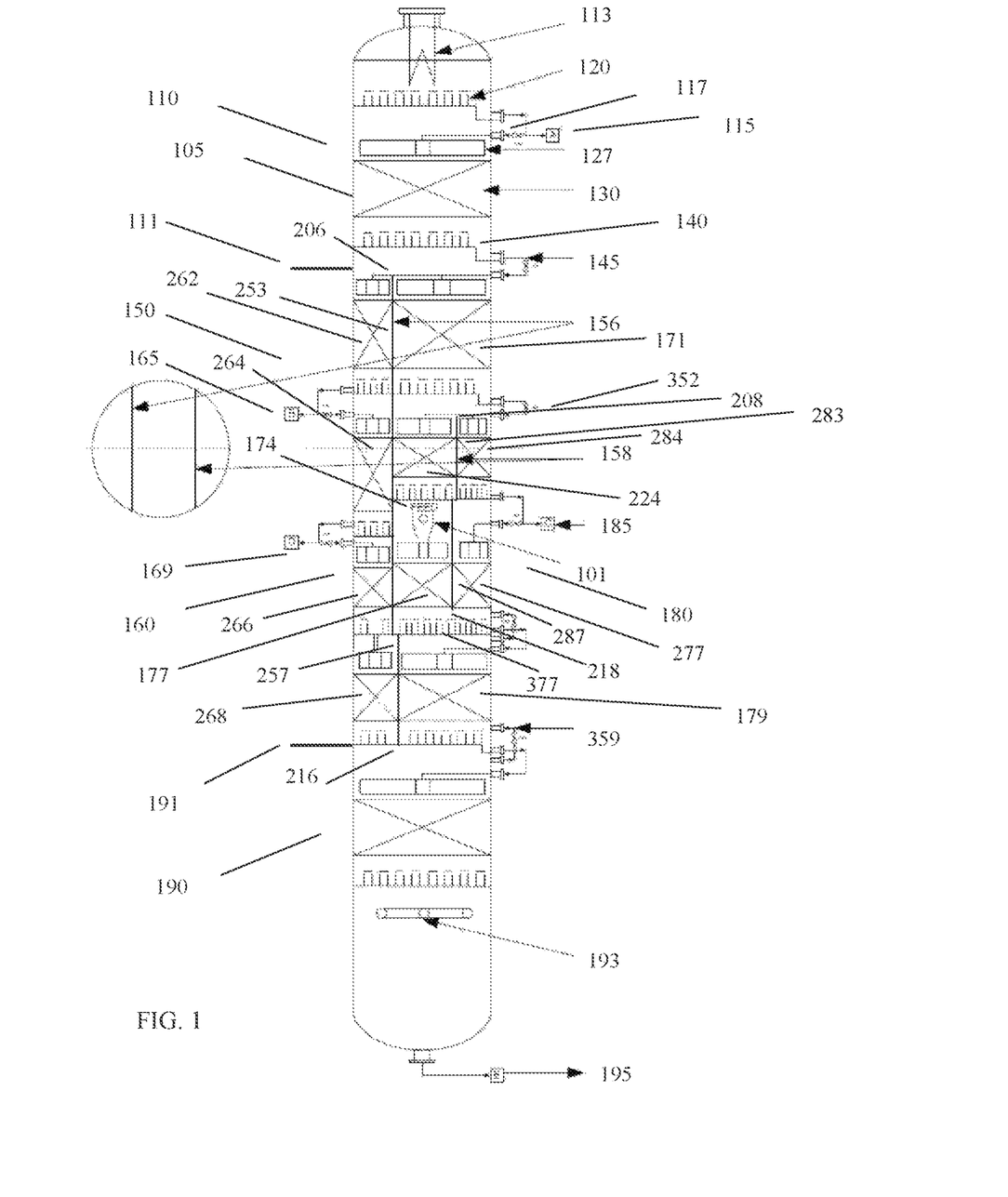
FIG. 1 shows an example of a dividing wall column configuration that allows for separation of at least five products from a feed while having two vapor splits and two liquid splits within the column.

FIG. 1 schematically shows an example of a configuration for a dividing wall column including two dividing walls. The dividing walls in FIG. 1 correspond to walls made from a plurality of wall segments, with at least one wall segment that is offset horizontally from other wall segments.

In FIG. 1, a fractionation column includes a top common volume 110, a bottom common volume 190, and a plurality of other volumes in an intermediate volume 150. The start of top common volume 110 is indicated by height indicator 111, while the start of bottom common volume 190 is indicated by height indicator 191.

Bottom common volume 190 includes a bottom product withdrawal 195 for providing a product stream that is at least partially sent to a reboiler (not shown) for heating to maintain the temperature of the fractionation column. The heated product stream is returned to the fractionation column via the reboiler return 193. Any convenient type of reboiler return 193 may be used, including but not limited to, a flush nozzle, a pipe distributor, a vane distributor, or a baffle distributor.

Top common volume 110 includes an optional embedded overhead condenser 113 and a top product withdrawal 115, for withdrawal of a lowest boiling product from the feedstock. Optionally, a plurality of product withdrawals for different boiling ranges can be included as part of top common volume 110. For the product withdrawals other than bottom product withdrawal 195, various additional internal structures can be associated with the product withdrawal location. For example, for top product withdrawal 115, the liquid for withdrawal is collected in a chimney tray 120. A portion of the liquid becomes product for withdrawal 115, while a remaining portion is returned 117 to a liquid distributor 127 to allow for further distillation. The liquid portion returned 117 to liquid distributor 127 passes downward into packed bed 130, where the liquid can contact upward-moving heated vapor. This can potentially cause some volatilization of the downward-moving liquid, while also potentially causing some condensation of the upward-moving vapor. The upward-moving vapor can continue moving upward until either the vapor condenses and is withdrawn as part of a product withdrawal or until the vapor exits through a gas phase withdrawal location (not shown). The downward-moving liquid that exits from the packed bed can drop into the next lower chimney tray 140 for possible withdrawal as part of product withdrawal 145. In the example shown in FIG. 1, two products can be withdrawn from the top common volume.

The processes of vapor moving upward and liquid moving downward also occur in the various divided volumes within the fractionation column. The example shown in FIG. 1 includes multiple divided volumes, each including a packed bed, a flow distributor above the packed bed, and a chimney tray/liquid withdrawal tray below the packed bed. The example in FIG. 1 also includes tower section 160, which corresponds to the tower section between dividing wall 156 and the vessel wall 105 (could also be referred to as column wall) of the fractionator, and tower section 180, which corresponds to the tower section between dividing wall 158 and vessel wall 105. It is noted that a top cross-sectional view of dividing walls 156 and 158 is also presented in FIG. 1. Tower section 160 includes divided volumes 262, 264, 266, and 268. In the example shown in FIG. 1, products can be withdrawn at withdrawal location 165 associated with divided volume 262, and at withdrawal location 169 associated with divided volume 264. Optionally, products could also be withdrawn from locations (not shown) associated with divided volumes 266 and 268. Tower section 180 includes divided volume 284. It is noted that packed bed 277 does not correspond to a divided volume, in part because chimney tray 377 receives liquid from both packed bed 277 and packed bed 177. By contrast, divided volume 179 does qualify as a divided volume, since the packed bed has an associated flow distributor and chimney tray that all share a common dividing wall.

In the example shown in FIG. 1, feed entry volume 174 corresponds to a volume where feedstock for separation is introduced into the column via feed inlet 101. Divided volumes 171 and 179 can optionally include product withdrawal locations, but in some preferred aspects, product withdrawals can be limited to divided volumes that are not in direct fluid communication with a volume that contains a feed inlet. For example, even though a withdrawal location 352 is available in divided volume 171, in the example shown in FIG. 1, the withdrawal location would be used to control the liquid split to each side of the dividing wall and not as an intermediate mixed product. Similarly, withdrawal location 359 could produce an intermediate product, but in FIG. 1 the withdrawal location 359 is used for flow regulation.

In FIG. 1, dividing wall 156 includes at least two wall sections 253 and 257, with wall section 257 being horizontally offset from wall section 253. Having wall section 257 offset toward the center of the column can provide additional volume for divided volume 266, based on the higher vapor loading that can be expected in lower portion of the side drawoff product sections of the column. Having substantially parallel wall sections that are horizontally offset can reduce or minimize waste volume and increase column volume utilization compared to having angled wall sections. Similarly, dividing wall 158 includes at least two wall sections 283 and 287.

As illustrated in FIG. 1, the internal structures within the column can differ on the opposite sides of a dividing wall. For example, the packed bed in divided volume 264 is shown as having a larger depth than the corresponding packed bed associated with divided volume 224 on the opposite side of dividing wall 156. As a result, the chimney tray associated with divided volume 264 is at a lower elevation than the corresponding chimney tray associated with divided volume 224 on the opposite side of dividing wall 156.

In the example shown in FIG. 1, dividing walls 156 and 158 have different total lengths, different top heights 206 and 208 relative to the column height, and different bottom heights 216 and 218 relative to the column height. In various aspects, any convenient dividing wall can have the highest top height and/or the lowest bottom height. It is noted that top heights 206 and 208 correspond to the liquid splits in the example shown in FIG. 1, while bottom heights 216 and 218 correspond to the vapor splits.

In FIG. 1, side drawoff products can be withdrawn from the column at withdrawal locations 165, 169, and 185. Optionally but preferably, the side drawoff product withdrawn at location 185 can have a boiling range that is between the boiling range for the side drawoff product withdrawn at location 165 and the side drawoff product withdrawn at location 169. By having a higher relative volatility in boiling ranges between the side drawoff products from locations 165 and 169, the packed bed associated with divided volume 264 can have a lower number of equivalent trays than would otherwise be needed for side drawoff products with adjacent boiling ranges.

VIII. Control Configuration Example

Figure 2:
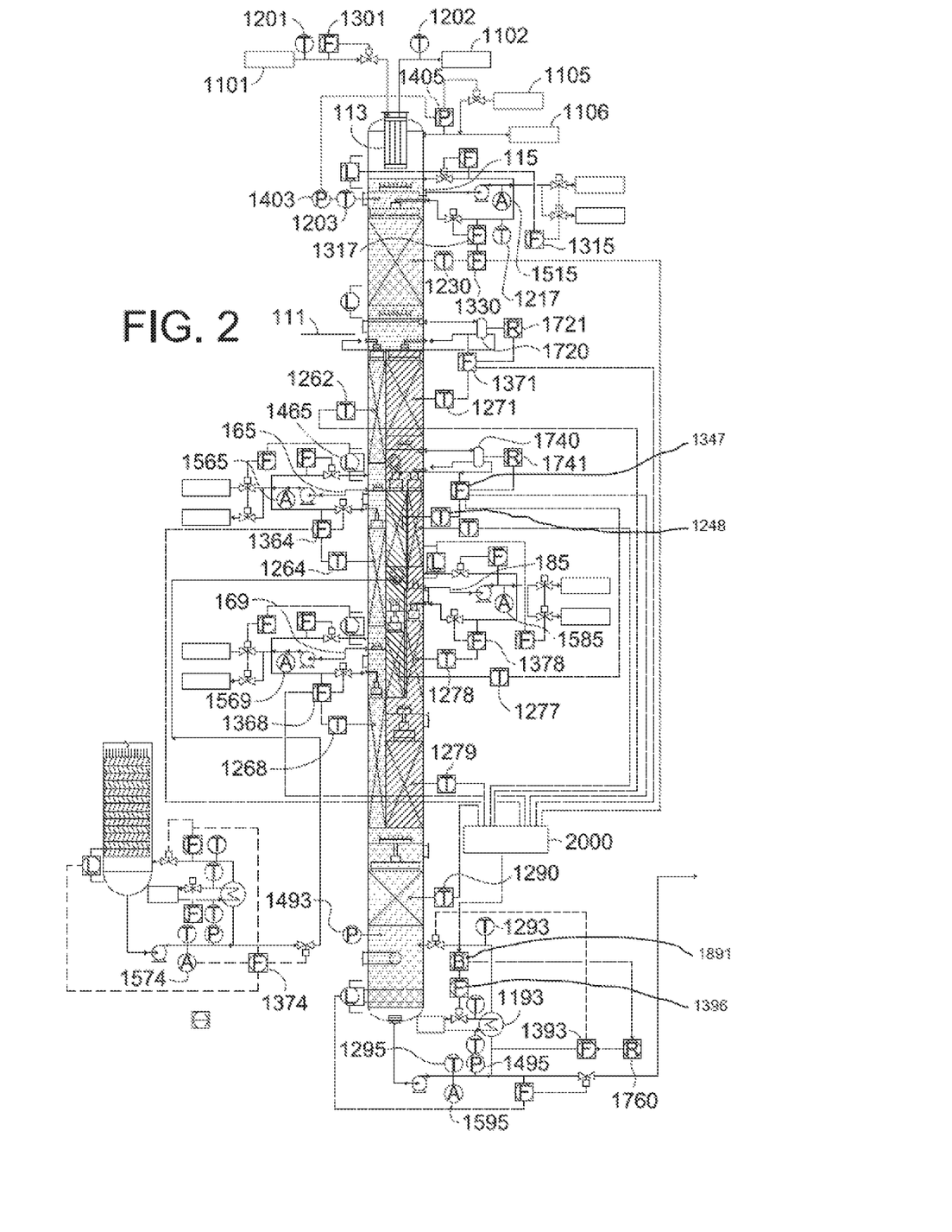
FIG. 2 shows an example of controller, sensors, and other analyzers that can be used in conjunction with a dividing wall column configuration similar to the configuration shown in FIG. 1.

FIG. 2 shows a similar DWC configuration for producing five distinct products. However, FIG. 2 provides additional information by indicating the process control structures associated with operation of the DWC. It is noted that in FIG. 2, symbols including the letter "T" correspond to temperature sensors/controllers; symbols including the letter "P" correspond to pressure sensors/controllers" symbols including the letter "L" correspond to level indicators or controllers' symbols including the letter "A" correspond to composition analyzers; symbols including the letter "F" correspond to flow sensors/controllers; and symbols including the letter "R" correspond to ratio controllers. For the temperature, pressure, flow, and reflux symbols, a controller is indicated by the use of a circle inside a box, while a sensor/indicator is indicated by the use of only a circle.

The top common volume 110 in FIG. 1 includes various components and controls for managing pressure and temperature in the column as well as managing the overhead product stream. A similar height indicator 111 is provided in FIG. 2 to indicate the boundary for top common volume 110.

Prior to entering the feed entry volume 174, the feed can be analyzed 1574 to characterize the composition of the feed, including the amount of light components that should be excluded from the feed vapor split and heavy components that should be excluded from the feed liquid split. The flow rate of feed can be controlled and/or monitored by flow controller 1374. Within feed entry volume 174, a temperature controller can provide the temperature corresponding to the top feed entry temperature (at least two theoretical stages below the liquid split). This can correspond to temperature controller 1248, or a separate temperature controller (not shown) can be used. For the bottom feed temperature (at least two theoretical stages above the vapor split), a temperature controller such as temperature controller 1277 can be used.

At the top of the configuration shown in FIG. 2, cooling water can be provided to condenser 113 by cooling water supply 1101, and then can exit to cooling water return 1102. The temperature of the cooling water provided by cooling water supply 1101 can be monitored by temperature indicator 1201. To manage temperature at the top of the column, flow controller 1301 can vary the amount of cooling water that is delivered to the condenser 113. Temperature indicator 1202 can be used to monitor the temperature of the cooling water after it exits from condenser 113.

The overhead pressure can be managed in part by using a combination of pressure control steam 1105 and vacuum system 1106. Steam injection into the column can be controlled by a pressure controller 1405, based in part on input received from pressure indicator 1403 and temperature indicator 1203.

Another portion of managing the overhead pressure and temperature can be provided based on the amount of overhead product that is withdrawn. In FIG. 1, the overhead product corresponds to product 115. The withdrawal of product 115 can be managed by a combination of several controllers and indicators. For example, in the configuration shown in FIG. 2, an analyzer 1515 can be used to characterize the composition of the product withdrawn from the column. Flow controller 1315 can control the amount of the product that is used as product and/or diverted to overflow storage. The remaining withdrawn product can then be returned as an external reflux stream, as managed by flow controller 1317. The amount of external flux can vary, depending on the desired amount of internal reflux that is needed to maintain energy balance for the products and the controlled temperature(s) in the upper section of the column. The amount of internal reflux can be calculated based in part on information provided by temperature indicator 1217 and flow controller 1317. The temperature controller 1230 resets the setpoint for the required internal reflux flow 1330 thereby using energy balance to stabilize the fractionation in packed bed 130

At the top of the first dividing wall, a reflux splitter 1720 can be included to assist with temperature and pressure management at the liquid split in order to maintain energy balance on the feed side of the dividing wall. Reflux splitter 1720 can receive a draw stream from the column and return a first portion of the stream above one side of the dividing wall while returning a second portion of the stream above the opposite side of the dividing wall. The "split" between the first portion and the second portion can be managed by reflux ratio controller 1721. In the configuration shown in FIG. 2, the setpoint for ratio controller 1721 can be selected in part based on information received from a flow controller 1371 that monitors the portion of the liquid flow going to the feed side of the dividing wall. The desired setpoint for flow controller 1371 can be processed as a constrained variable by a constraint selector 2000. The information relevant to constraint selector 2000 can include, but is not limited to, information from flow controller 1371 and temperature controller 1262, which provides temperature information on the other side of the dividing wall and information from temperature controller 1279.

A reflux splitter 1740 is also included to assist with maintaining a desired temperature below the liquid split of the dividing wall 158 in the feed entry volume 174. Reflux splitter 1740 can receive a draw stream from the column and return a first portion of the stream above feed entry volume 174 while returning a second portion of the stream above the opposite side of the dividing wall. The "split" performed in reflux splitter 1740 can be managed by reflux ratio controller 1741. The setpoint for reflux ratio controller 1741 can be selected in part based on information received from a flow controller 1347 that monitors the portion of the flow delivered above feed entry volume 174. In the configuration shown in FIG. 2, the desired setpoint for flow controller 1347 can be selected from temperature controller 1277. Without being bound by any particular theory, by using the bottom feed entry temperature (as detected by temperature controller 1277) to assist with selecting the reflux split for reflux splitter 1740, an increased amount of interaction can occur between the internal reflux on the feed side of the wall with the upward-moving fluids on the feed side of the wall. By contrast, if the reflux splitter is controlled based on the top feed entry temperature (as detected by temperature controller 1248), a more limited amount of interaction will occur between the reflux and upward moving gases prior to sampling the temperature. This could result in a more limited feedback response.

In addition to reflux splitter 1720 and reflux splitter 1740, other reflux loops can be used to manage the cut point temperature associated with various product withdrawal locations. For example, for product 2 (reference numeral 165, corresponding to the lightest intermediate product), after analysis of the withdrawn stream by analyzer 1565, a portion of the withdrawn stream can be returned as reflux below the withdrawal location. In the example shown in FIG. 2, the reflux below the withdrawal location for product 2 (165) can be controlled by flow controller 1364, based in part on temperature information provided by temperature controller 1264 and/or analyzer 1565. It is noted that analyzer 1565 can provide information regarding product quality. If the composition analyzed by analyzer 1565 does not match a desired compositional profile, the set point of flow controller 1364 can be modified to assist with adjusting the temperature at the cut point location for product 2. For example, if the composition of product 2 includes too many heavy components, additional reflux can be used to reduce the temperature at the cut point location 1264.

Similar control schemes can be used to manage the temperature and/or the compositional profile at the withdrawal locations for the other intermediate products shown in FIG. 2, corresponding to product 3 (reference numeral 185) and product 4 (reference numeral 169). For product 3 (185), after analysis of the withdrawn stream by analyzer 1585, a portion of the withdrawn stream can be returned as reflux below the withdrawal location. In the example shown in FIG. 2, the reflux below the withdrawal location for product 3 (185) can be controlled by flow controller 1378, based in part on temperature information provided by temperature controller 1278 and/or analyzer 1585. Similarly, for product 4 (169), after analysis of the withdrawn stream by analyzer 1569, a portion of the withdrawn stream can be returned as reflux below the withdrawal location. In the example shown in FIG. 2, the reflux below the withdrawal location for product 4 (169) can be controlled by flow controller 1368, based in part on temperature information provided by temperature controller 1268 and/or analyzer 1569.

The primary heat source for the column is provided by the reboiler loop heater 1193 in the bottom section of the column. After withdrawing a bottoms stream, the composition of the bottoms stream can be analyzed 1595, the temperature can be determined by one or more sensors 1295, and the pressure can be determined by one or more sensors 1495. A portion of the bottoms stream can then be passed out as a product stream, while a second portion is passed through heater 1193 for reboiling and subsequent return to the column. The temperature of the heated return stream can be determined by a sensor 1293. The flow rate of the heated return stream can be controlled by flow controller 1393, based on a setpoint provided by ratio controller 1760. The duty cycle for the reboiler can be selected, for example, by constraint selector 2000. The constraint selector 2000 can provide a setpoint for boiler control 1891, which can provide a setpoint for a flow controller 1396.

In some aspects, the desired temperatures for each product cut point, the column bottom temperature, and the column overhead temperature can all be controlled separately. In other aspects, a multivariable controller can be used to manage various temperatures within the column. For example, in a conventional distillation column, the duty cycle for heater 1193 would be determined based on a desired bottoms temperature, such as a setpoint temperature for a controller in the vicinity of temperature controller 1290. However, basing the reboiler duty cycle on only the bottoms temperature could result in insufficient heat for fractionation higher in the column. In order to overcome this difficulty, temperatures and flows from various locations in the column can be passed into constraint selector 2000. Constraint selector 2000 can then monitor the various temperatures and flows higher up in the column. The reboiler duty can then be selected so that all of the monitored temperatures and flows are sufficient for the desired separation. This may require introducing additional energy into the column, as a higher duty cycle may be needed than what would be required to achieve the desired bottoms separation. To the degree that some excess heat may be present in the system due to operating the reboiler at a higher duty cycle, a multivariable controller can also adjust various reflux splitters and/or product reflux loops to maintain desired temperatures at the various locations. This can allow energy balance to be maintained within the column, so that the product draws can have a desired composition while also maintaining desired target temperatures within the feed entry volume.

In the configuration shown in FIG. 2, constraint selector 2000 receives information from 10 different groups of temperature controllers and/or flow controllers. This allows the constraint selector to receive temperature information from throughout the various elevations in the distillation column. Based on the received temperature information, the constraint selector 2000 can select a duty cycle for reboiler heater 1193 so that sufficient energy is available to reach all target temperatures in the column. Optionally, the multivariable controller can also receive information from feed analyzer 1574 and/or feed flow controller 1374 to provide forward information regarding changes to the input feed. This can allow a multivariable controller to adjust setpoints for temperature and/or pressure at various locations based on changes in feed composition and/or feed rate. In the example shown in FIG. 2, the feed into the column corresponds to a bottoms fraction from a prior vessel, such as a bottoms fraction from a prior fractionation column.

ADDITIONAL EMBODIMENTS

Embodiment 1

A method for separating a feed into a plurality of products, comprising: passing a feed comprising i) 1 vol % or more of one or more light components, ii) 1 vol % or more of one or more heavy components, or iii) a combination of i) and ii), into a feed entry volume defined by a first dividing wall and a second dividing wall in a distillation column, the feed entry volume being in fluid communication with a top common volume and in fluid communication with a bottom common volume; maintaining, during the passing, a bottom feed entry temperature within the feed entry volume between a first temperature and a second temperature, the bottom feed entry temperature being measured at a location at least two theoretical stages above a feed vapor split, the first temperature and the second temperature being greater than a final boiling point of the one or more light components; maintaining, during the passing, a top feed entry temperature within the feed entry volume between a third temperature and a fourth temperature, the top feed entry temperature being measured at a location at least two theoretical stages below a feed liquid split, the third temperature and the fourth temperature being less than an initial boiling point of the one or more heavy components; withdrawing, from a first divided volume of the distillation column, a first product stream, the first divided volume being located in a first tower section defined in part by the first dividing wall, the first product stream comprising at least a portion of the one or more light components; withdrawing, from a second divided volume of the distillation column, a second product which is less volatile based on normal boiling point than the first product stream, the second divided volume being located in a second tower section defined in part by the second dividing wall; withdrawing, from a third divided volume of the distillation column, a third product stream which is less volatile based on normal boiling point than the second product stream, the third divided volume being located in the first tower section, the third product stream comprising at least a portion of the one or more heavy components; withdrawing, from the bottom common volume, a bottom product stream; and withdrawing a top product stream from above a top packed bed of the distillation column, wherein a concentration of the one or more light components at the feed vapor split is less than 0.1 vol % and a concentration of the one or more heavy components at the feed liquid split is less than 0.1 vol %.

Embodiment 2

A method for separating a feed into a plurality of products, comprising: passing a feed comprising i) 1 vol % or more of one or more light components, ii) 1 vol % or more of one or more heavy components, or iii) a combination of i) and ii), into a feed entry volume defined by a first dividing wall and a second dividing wall in a distillation column, the feed entry volume being in fluid communication with a top common volume and in fluid communication with a bottom common volume; maintaining, during the passing, a bottom feed entry temperature within the feed entry volume between a first temperature and a second temperature, the bottom feed entry temperature being measured at a location at least two theoretical stages above a feed vapor split, the first temperature and the second temperature being greater than a final boiling point of the one or more light components; maintaining, during the passing, a top feed entry temperature within the feed entry volume between a third temperature and a fourth temperature, the top feed entry temperature being measured at a location at least two theoretical stages below a feed liquid split, the third temperature and the fourth temperature being less than an initial boiling point of the one or more heavy components; withdrawing, from a first divided volume of the distillation column, a first product stream, the first divided volume being located in a first tower section defined in part by the first dividing wall, the first product stream comprising at least a portion of the one or more light components; withdrawing, from a second divided volume of the distillation column, a second product which is less volatile based on normal boiling point than the first product stream, the second divided volume being located in a second tower section defined in part by the second dividing wall, the second product stream comprising at least a portion of the one or more heavy components; withdrawing, from the bottom common volume, a bottom product stream; and withdrawing a top product stream from above a top packed bed of the distillation column, wherein a concentration of the one or more light components at the feed vapor split is less than 0.1 vol % and a concentration of the one or more heavy components at the feed liquid split is less than 0.1 vol %.

Embodiment 3

A method for separating a feed into a plurality of products, comprising: passing a feed comprising i) 1 vol % or more of one or more light components, ii) 1 vol % or more of one or more heavy components, or iii) a combination of i) and ii), into a feed entry volume defined by a first dividing wall and a second dividing wall in a distillation column, the feed entry volume being in fluid communication with a top common volume and in fluid communication with a bottom common volume; maintaining, during the passing, a bottom feed entry temperature within the feed entry volume between a first temperature and a second temperature, the bottom feed entry temperature being measured at a location at least two theoretical stages above a feed vapor split, the first temperature and the second temperature being greater than a final boiling point of the one or more light components; maintaining, during the passing, a top feed entry temperature within the feed entry volume between a third temperature and a fourth temperature, the top feed entry temperature being measured at a location at least two theoretical stages below a feed liquid split, the third temperature and the fourth temperature being less than an initial boiling point of the one or more heavy components; withdrawing, from a first divided volume of the distillation column, a first product stream, the first divided volume being located in a first tower section defined in part by the first dividing wall, the first product stream comprising at least a portion of the one or more light components; withdrawing, from a second divided volume of the distillation column, a second product which is less volatile based on normal boiling point than the first product stream, the second divided volume being located in a second tower section defined in part by the second dividing wall; withdrawing, from a third divided volume of the distillation column, a third product stream which is less volatile based on normal boiling point than the second product stream, the third divided volume being located in the first tower section; withdrawing, from a fourth divided volume of the distillation column, a fourth product stream which is less volatile based on normal boiling point than the third product stream, the fourth divided volume being located in the second tower section, the fourth product stream comprising at least a portion of the one or more heavy components; withdrawing, from the bottom common volume, a bottom product stream; and withdrawing a top product stream from above a top packed bed of the distillation column, wherein a concentration of the one or more light components at the feed vapor split is less than 0.1 vol % and a concentration of the one or more heavy components at the feed liquid split is less than 0.1 vol %.

Embodiment 4

The method of any of the above embodiments, wherein an interior of the distillation column comprises two or less liquid splits and two or less vapor splits.

Embodiment 5

The method of any of the above embodiments, wherein the feedstock comprises 10 vol % or more of the one or more light components, or wherein the feedstock comprises 10 vol % or more of the one or more heavy components, or a combination thereof.

Embodiment 6

The method of any of the above embodiments, wherein at least one of the bottom feed entry temperature and the top feed entry temperature comprises a pressure compensated temperature.

Embodiment 7

The method of any of the above embodiments, the method further comprising: withdrawing a feed reflux draw above the feed liquid split; splitting the feed reflux draw in a feed reflux splitter to form at least a first portion of the feed reflux draw and a second portion of the feed reflux draw, the splitting being based on a feed reflux splitter position; returning a first portion of the feed reflux draw above a feed side of the feed liquid split; and returning a second portion of the feed reflux draw above a product side of the feed liquid split.

Embodiment 8

The method of Embodiment 7, wherein maintaining the bottom feed entry temperature comprises: measuring the bottom feed entry temperature; determining a flow rate of the returned first portion of the feed reflux draw; and modifying the feed reflux splitter position to maintain the bottom feed entry temperature between the third temperature and the fourth temperature based on the measured bottom feed entry temperature and the determined flow rate of the returned first portion of the feed reflux draw.

Embodiment 9

The method of any of the above embodiments, wherein maintaining the bottom feed entry temperature further comprises: measuring a flow rate of the feed; analyzing the feed to determine an amount of the one or more light components, the one or more heavy components, or a combination thereof; and modifying a setpoint for the bottom feed entry temperature based on the measured flow rate, the analyzed amount of the one or more light components, the analyzed amount of the one or more heavy components, or a combination thereof.

Embodiment 10

The method of any of the above embodiments, wherein maintaining the top feed entry temperature comprises: measuring the top feed entry temperature; and modifying an overhead temperature based on control of an overhead internal reflux to maintain the top feed entry temperature between the first temperature and the second temperature.

Embodiment 11

The method of any of the above embodiments, wherein maintaining the bottom feed temperature, the top feed temperature, or a combination thereof, comprises: passing at least one of the measured bottom feed entry temperature and the measured top feed entry temperature into a multivariable controller; passing a plurality of additional measured values into the multivariable controller, the plurality of additional measured values comprising at least the determined feed flow rate; and modifying at least one of a feed reflux draw, a feed reflux splitter position, and a reboiler duty based on one or more of the measured bottom feed entry temperature, the measured top feed entry temperature, the determined feed flow rate, and an additional measured value.

Embodiment 12

The method of Embodiment 11, wherein the plurality of additional measured values comprise one or more product temperatures associated with the top product stream, the bottom product stream, the first product stream, the second product stream, and the third product stream, and wherein at least one of a top internal reflux and the reboiler duty is modified based on the one or more product temperatures.

Embodiment 13

The method of any of the above embodiments, wherein withdrawing the first product stream further comprises: determining a setpoint for a first withdrawal tray temperature, a first withdrawal tray draw rate, or a combination thereof; maintaining the first withdrawal tray temperature based on at least the determined setpoint for the first withdrawal tray temperature and two or more of a first withdrawal tray top reflux, a first withdrawal tray bottom reflux, and the first withdrawal tray draw rate.

Embodiment 14

The method of Embodiment 13, further comprising: measuring a plurality temperatures of a withdrawal stream from the first withdrawal tray; and modifiying the setpoint for the first withdrawal tray temperature, the first withdrawal tray draw rate, or a combination thereof based on the plurality of measured temperatures of the withdrawal stream from the first withdrawal tray.

Embodiment 15

The method of any of the above embodiments, wherein withdrawing the second product stream further comprises: determining a setpoint for a second withdrawal tray temperature, a second withdrawal tray draw rate, or a combination thereof; maintaining the second withdrawal tray temperature based on at least the determined setpoint for the second withdrawal tray temperature and two or more of a second withdrawal tray top reflux, a second withdrawal tray bottom reflux, and the second withdrawal tray draw rate.

Embodiment 16

The method of Embodiment 15, further comprising: measuring a plurality temperatures of a withdrawal stream from the second withdrawal tray; and modifiying the setpoint for the second withdrawal tray temperature, the second withdrawal tray draw rate, or a combination thereof based on the plurality of measured temperatures of the withdrawal stream from the second withdrawal tray.

Embodiment 17

The method of any of Embodiments 1 or 3-16, wherein withdrawing the third product stream further comprises: determining a setpoint for a third withdrawal tray temperature, a third withdrawal tray draw rate, or a combination thereof; maintaining the third withdrawal tray temperature based on at least the determined setpoint for the third withdrawal tray temperature and two or more of a third withdrawal tray top reflux, a third withdrawal tray bottom reflux, and the third withdrawal tray draw rate.

Embodiment 18

The method of Embodiment 17, further comprising: measuring a plurality temperatures of a withdrawal stream from the third withdrawal tray; and modifiying the setpoint for the third withdrawal tray temperature, the third withdrawal tray draw rate, or a combination thereof based on the plurality of measured temperatures of the withdrawal stream from the third withdrawal tray.

Embodiment 19

The method of any of the above embodiments, wherein analyzing the feed comprises sampling the feed to acquire a sample, and analyzing the sample using a gas chromatograph.

Embodiment 20

The method of any of the above embodiments, further comprising: determining a target overhead temperature in the distillation column; and maintaining the target overhead temperature based on modification of an internal reflux.

Embodiment 21

The method of any of Embodiments 1 or 4-20, further comprising withdrawing, from a fourth divided volume of the distillation column, a fourth product stream which is less volatile based on normal boiling point than the third product stream, the fourth divided volume being located in the second tower section.

Embodiment 22

The method of any of the above embodiments, wherein at least one of the first dividing wall and the second dividing wall comprises a plurality of substantially parallel dividing wall sections, at least one dividing wall section of the plurality of substantially parallel dividing wall sections being horizontally offset from at least one other dividing wall section of the plurality of substantially parallel dividing wall sections.

Embodiment 23

A system for separating a feed into a plurality of products, comprising: a distillation column comprising a top common volume, a bottom common volume, an intermediate volume, and a column wall; a reboiler comprising a reboiler duty controller in the bottom common volume; a first dividing wall and a second dividing wall in the intermediate volume, the first dividing wall and the second dividing wall defining a feed entry volume, a feed vapor split, and a feed liquid split, the first dividing wall and the column wall defining a first tower section comprising a first plurality of divided volumes, the second dividing wall and the column wall defining a second tower section comprising a second plurality of divided volumes; a first reflux splitter in fluid communication with the top common volume via a reflux draw, a first reflux return above the first tower section, and a second reflux return above the second tower section; a feed reflux splitter in fluid communication with the distillation column in a volume above the feed liquid split via a feed reflux draw, a first feed reflux return above the feed entry volume, and a second feed reflux return; a feed entry top temperature sensor located at least two theoretical stages below the feed liquid split; a feed entry bottom temperature sensor located at least two theoretical stages above the feed vapor split; a feed inlet in fluid communication with the feed entry volume, the feed inlet including a feed analyzer; at least one top outlet in fluid communication with the top common volume or with a volume above a top packed bed; at least one bottom outlet in fluid communication with the bottom common volume; a first outlet in fluid communication with a first divided volume of the first plurality of divided volumes; a second outlet in fluid communication with a second divided volume of the second plurality of divided volumes; a third outlet in fluid communication with a third divided volume of the first plurality of divided volumes, an elevation of the third outlet being lower than an elevation of the first outlet; and a multivariable controller in receiving communication with at least the feed top entry temperature sensor, the feed bottom entry temperature sensor, the feed analyzer, the multivariable controller configured to provide input communication to at least one of the reboiler duty controller, a feed reflux draw controller, and a feed reflux splitter based on one or more of a feed top entry temperature, a feed bottom entry temperature, and an analyzed feed composition.

Embodiment 24

The system of Embodiment 23, wherein the multivariable controller is further in receiving communication with a plurality of additional temperature sensors comprising a first outlet temperature sensor, a second outlet temperature sensor, a third outlet temperature sensor, a top outlet temperature sensor, and a bottom outlet temperature sensor, the multivariable controller being configured to provide input communication to the reboiler duty controller based on one or more additional temperature sensors.

Embodiment 25

The system of Embodiment 23 or 24, wherein the multivariable controller is further in receiving communication with a feed top pressure sensor and a feed bottom pressure sensor, the control of at least one of the top feed entry temperature and the bottom feed entry temperature being based on a pressure-sensitive temperature.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for separating a feed into a plurality of products, comprising:

passing a feed comprising 1 vol % or more of one or more light components, and 1 vol % or more of one or more heavy components into a feed entry volume defined by a first dividing wall and a second dividing wall in a distillation column, the feed entry volume being in fluid communication with a top common volume and in fluid communication with a bottom common volume;

maintaining, during the passing, a bottom feed entry temperature within the feed entry volume between a first temperature and a second temperature, the bottom feed entry temperature being measured at a location at least two theoretical stages above a feed vapor split, the first temperature and the second temperature being greater than a final boiling point of the one or more light components;

maintaining, during the passing, a top feed entry temperature within the feed entry volume between a third temperature and a fourth temperature, the top feed entry temperature being measured at a location at least two theoretical stages below a feed liquid split, the third temperature and the fourth temperature being less than an initial boiling point of the one or more heavy components;

withdrawing, from a first divided volume of the distillation column, a first product stream, the first divided volume being located in a first tower section defined in part by the first dividing wall, the first product stream comprising at least a portion of the one or more light components;

withdrawing, from a second divided volume of the distillation column, a second product stream which is less volatile based on normal boiling point than the first product stream, the second divided volume being located in a second tower section defined in part by the second dividing wall;

withdrawing, from a third divided volume of the distillation column, a third product stream which is less volatile based on normal boiling point than the second product stream, the third divided volume being located in the first tower section, the third product stream comprising at least a portion of the one or more heavy components;

withdrawing, from the bottom common volume, a bottom product stream; and withdrawing a top product stream from above a top packed bed of the distillation column, wherein a concentration of the one or more light components at the feed vapor split is less than 0.1 vol % and a concentration of the one or more heavy components at the feed liquid split is less than 0.1 vol %.

2. The method of claim 1, wherein an interior of the distillation column comprises two or less liquid splits and two or less vapor splits.

3. The method of claim 1, wherein the feedstock comprises 10 vol % or more of the one or more light components, or wherein the feedstock comprises 10 vol % or more of the one or more heavy components, or a combination thereof.

4. The method of claim 1, wherein at least one of the bottom feed entry temperature and the top feed entry temperature comprises a pressure compensated temperature.

5. The method of claim 1, the method further comprising:
withdrawing a feed reflux draw above the feed liquid split;
splitting the feed reflux draw in a feed reflux splitter to form at least a first portion of the feed reflux draw and a second portion of the feed reflux draw, the splitting being based on a feed reflux splitter position;
returning the first portion of the feed reflux draw above a feed side of the feed liquid split; and
returning the second portion of the feed reflux draw above a product side of the feed liquid split.

6. The method of claim 5, wherein maintaining the bottom feed entry temperature comprises:
measuring the bottom feed entry temperature;
determining a flow rate of the returned first portion of the feed reflux draw; and
modifying the feed reflux splitter position to maintain the bottom feed entry temperature between the third temperature and the fourth temperature based on the measured bottom feed entry temperature and the determined flow rate of the returned first portion of the feed reflux draw.

7. The method of claim 1, wherein maintaining the bottom feed entry temperature further comprises:
measuring a flow rate of the feed;
analyzing the feed to determine an amount of the one or more light components, the one or more heavy components, or a combination thereof; and
modifying a setpoint for the bottom feed entry temperature based on the measured flow rate, the analyzed amount of the one or more light components, the analyzed amount of the one or more heavy components, or a combination thereof.

8. The method of claim 1, wherein maintaining the top feed entry temperature comprises:
measuring the top feed entry temperature; and
modifying an overhead temperature based on control of an overhead internal reflux to maintain the top feed entry temperature between the first temperature and the second temperature.

9. The method of claim 1, wherein maintaining the bottom feed temperature, the top feed temperature, or a combination thereof, comprises:
passing at least one of the measured bottom feed entry temperature and the measured top feed entry temperature into a multivariable controller;
passing a plurality of additional measured values into the multivariable controller, the plurality of additional measured values comprising at least a determined feed flow rate; and
modifying at least one of a feed reflux draw, a feed reflux splitter position, and a reboiler duty based on one or more of the measured bottom feed entry temperature, the measured top feed entry temperature, the determined feed flow rate, and an additional measured value.

10. The method of claim 9, wherein the plurality of additional measured values comprises one or more product temperatures associated with the top product stream, the bottom product stream, the first product stream, the second product stream, and the third product stream, and
wherein at least one of a top internal reflux and the reboiler duty is modified based on the one or more product temperatures.

11. The method of claim 1, wherein withdrawing the first product stream further comprises:
determining a setpoint for a first withdrawal tray temperature;
maintaining the first withdrawal tray temperature based on at least the determined setpoint for the first withdrawal tray temperature and two or more of a first withdrawal tray top reflux, a first withdrawal tray bottom reflux, and the first withdrawal tray draw rate.

12. The method of claim 11, further comprising:
measuring a plurality of temperatures of a withdrawal stream from the first withdrawal tray; and
modifying the setpoint for the first withdrawal tray temperature, the first withdrawal tray draw rate, or a combination thereof based on the plurality of measured temperatures of the withdrawal stream from the first withdrawal tray.

13. The method of claim 7, wherein analyzing the feed comprises sampling the feed to acquire a sample, and analyzing the sample using a gas chromatograph.

14. The method of claim 1, further comprising:
determining a target overhead temperature in the distillation column; and
maintaining the target overhead temperature based on modification of an internal reflux.

15. The method of claim 1, further comprising withdrawing, from a fourth divided volume of the distillation column, a fourth product stream which is less volatile based on normal boiling point than the third product stream, the fourth divided volume being located in the second tower section.

16. The method of claim 1, wherein at least one of the first dividing wall and the second dividing wall comprises a plurality of substantially parallel dividing wall sections, at least one dividing wall section of the plurality of substantially parallel dividing wall sections being horizontally offset from at least one other dividing wall section of the plurality of substantially parallel dividing wall sections.

17. A method for separating a feed into a plurality of products, comprising:
passing a feed comprising 1 vol % or more of one or more light components, and 1 vol % or more of one or more heavy components into a feed entry volume defined by a first dividing wall and a second dividing wall in a distillation column, the feed entry volume being in fluid communication with a top common volume and in fluid communication with a bottom common volume;

maintaining, during the passing, a bottom feed entry temperature within the feed entry volume between a first temperature and a second temperature, the bottom feed entry temperature being measured at a location at least two theoretical stages above a feed vapor split, the first temperature and the second temperature being greater than a final boiling point of the one or more light components;

maintaining, during the passing, a top feed entry temperature within the feed entry volume between a third temperature and a fourth temperature, the top feed entry temperature being measured at a location at least two theoretical stages below a feed liquid split, the third temperature and the fourth temperature being less than an initial boiling point of the one or more heavy components;

withdrawing, from a first divided volume of the distillation column, a first product stream, the first divided volume being located in a first tower section defined in part by the first dividing wall, the first product stream comprising at least a portion of the one or more light components;

withdrawing, from a second divided volume of the distillation column, a second product stream which is less volatile based on normal boiling point than the first product stream, the second divided volume being located in a second tower section defined in part by the second dividing wall;

withdrawing, from a third divided volume of the distillation column, a third product stream which is less volatile based on normal boiling point than the second product stream, the third divided volume being located in the first tower section;

withdrawing, from a fourth divided volume of the distillation column, a fourth product stream which is less volatile based on normal boiling point than the third product stream, the fourth divided volume being located in the second tower section, the fourth product stream comprising at least a portion of the one or more heavy components;

withdrawing, from the bottom common volume, a bottom product stream; and withdrawing a top product stream from above a top packed bed of the distillation column, wherein a concentration of the one or more light components at the feed vapor split is less than 0.1 vol % and a concentration of the one or more heavy components at the feed liquid split is less than 0.1 vol %.

18. A system for separating a feed into a plurality of products, comprising:
a distillation column comprising a top common volume, a bottom common volume, an intermediate volume, and a column wall;
a reboiler comprising a reboiler duty controller in the bottom common volume;
a first dividing wall and a second dividing wall in the intermediate volume, the first dividing wall and the second dividing wall defining a feed entry volume, a feed vapor split, and a feed liquid split, the first dividing wall and the column wall defining a first tower section comprising a first plurality of divided volumes, the second dividing wall and the column wall defining a second tower section comprising a second plurality of divided volumes;
a first reflux splitter in fluid communication with the top common volume via a reflux draw, a first reflux return above the first tower section, and a second reflux return above the second tower section;
a feed reflux splitter in fluid communication with the distillation column in a volume above the feed liquid split via a feed reflux draw, a first feed reflux return above the feed entry volume, and a second feed reflux return;
a feed top temperature sensor located at least two theoretical stages below the feed liquid split;
a feed bottom temperature sensor located at least two theoretical stages above the feed vapor split;
a feed inlet in fluid communication with the feed entry volume, the feed inlet including a feed analyzer;
at least one top outlet in fluid communication with the top common volume or with a volume above a top packed bed;
at least one bottom outlet in fluid communication with the bottom common volume;
a first outlet in fluid communication with a first divided volume of the first plurality of divided volumes;
a second outlet in fluid communication with a second divided volume of the second plurality of divided volumes;
a third outlet in fluid communication with a third divided volume of the first plurality of divided volumes, an elevation of the third outlet being lower than an elevation of the first outlet; and
a multivariable controller in receiving communication with at least the feed top temperature sensor, the feed bottom temperature sensor, the feed analyzer, the multivariable controller configured to provide input communication to at least one of the reboiler duty controller, a feed reflux draw controller, and a feed reflux splitter based on one or more of a feed top entry temperature, a feed bottom entry temperature, and an analyzed feed composition.

19. The system of claim 18, wherein the multivariable controller is further in receiving communication with a plurality of additional temperature sensors comprising a first outlet temperature sensor, a second outlet temperature sensor, a third outlet temperature sensor, a top outlet temperature sensor, and a bottom outlet temperature sensor, the multivariable controller being configured to provide input communication to the reboiler duty controller based on one or more additional temperature sensors.

20. The system of claim 18, wherein the multivariable controller is further in receiving communication with a feed top pressure sensor and a feed bottom pressure sensor, the control of at least one of the top feed entry temperature and the bottom feed entry temperature being based on a pressure-sensitive temperature.

* * * * *